US Patent Number: 4,728,649
Date of Patent: Mar. 1, 1988

Mantegani et al.

[54] 3-OXO-PIPERAZIN-1-YL-ERGOLINES EXHIBITING ANTIDOPAMINERGIC ACTIVITY

[75] Inventors: Sergio Mantegani; Aldemio Temperilli, both of Milan; Gabriella Traquandi, Cornate D'Adda; Alessandro Rossi; Lorenzo Pegrassi, both of Milan, all of Italy

[73] Assignee: Farmitalia Carlo Erba, Milan, Italy

[21] Appl. No.: 817,135

[22] Filed: Jan. 8, 1986

[30] Foreign Application Priority Data

Jan. 16, 1985 [GB] United Kingdom ............. 8501078

[51] Int. Cl.$^4$ ............... A61K 31/445; C07D 457/02
[52] U.S. Cl. ............................. 514/253; 514/254; 544/349; 544/361
[58] Field of Search ............. 544/361, 349; 514/253, 514/254

[56] References Cited

U.S. PATENT DOCUMENTS 3,583,991 6/1971 Troxler et al. ............. 546/69
4,252,941 2/1981 Mantegani et al. ............. 544/125
4,321,381 3/1982 Mantegani et al. ............. 546/67

FOREIGN PATENT DOCUMENTS 0126968 12/1984 European Pat. Off. .
1901750 9/1969 Fed. Rep. of Germany .
3000901 8/1980 Fed. Rep. of Germany .
615181 1/1980 Switzerland .

*Primary Examiner*—Donald G. Daus
*Assistant Examiner*—C. Shen
*Attorney, Agent, or Firm*—Oblon, Fisher, Spivak, McClelland & Maier

[57] ABSTRACT

The invention relates to ergoline derivatives having the general formula (I):

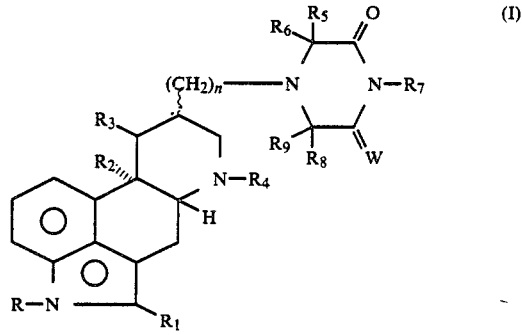

where $R=H$, $CH_3$; $R_1=H$, halogen, $CH_3$, phenylthio, $C_1$-$C_4$ alkylthio; $R_2=H$, $CH_3O$, and $R_3=H$ or $R_2+R_3=$chemical bond; $R_4=C_1$-$C_4$ hydrocarbon; $R_5$, $R_6$, $R_8$, $R_9$ independently$=H$, $C_1$-$C_4$ alkyl, or $R_5$, $R_8$ independently$=H$, $C_1$-$C_4$ alkyl and $R_6+R_9=CH_2CH_2$, $CH_2CH_2CH_2$; $R_7=H$, $C_1$-$C_4$ alkyl, phenyl, $NR'R''$; $R'$,$R''$ independently$=H$, $C_1$-$C_4$ alkyl, acyl or $NR'R''=$heterocyclic ring; $W=O$, $H_2$; $n=0$, 1, 2, and their pharmaceutically acceptable salts, these compounds exhibiting antihypertensive activity making them useful anxiolytic and antipsychotic agents. A process for their preparation and pharmaceutical compositions containing them are also described.

16 Claims, No Drawings

3-OXO-PIPERAZIN-1-YL-ERGOLINES EXHIBITING ANTIDOPAMINERGIC ACTIVITY

BACKGROUND OF THE INVENTION

1. Field of the Invention

This invention relates to ergoline derivatives, to processes for their preparation, and to pharmaceutical compositions containing them.

2. Discussion of the Background

A variety of semi-synthetic ergot derivatives have been prepared and shown to possess anti-hypertensive and other activities. See, for example, U.S. Pat. Nos. 4,252,941 and 4,321,381. Also, numerous derivatives are described in Kirk-Othmer's Encyclopedia of Chemical Technology, Vol. 1 (John Wiley & Sons, 1978). However, none of these derivatives has a piperazine moiety located on the ergoline derivative in the manner of the present invention.

SUMMARY OF THE INVENTION

It is an object of the present invention to provide compounds which are ergoline derivatives possessing a substituted piperazine moiety.

It is also an object of this invention to provide a method for preparing these ergoline derivatives.

Moreover, it is also an object of the present invention to provide pharmaceutical formulations containing ergoline derivatives possessing pharmacological activities. Further, it is an object of this invention to provide a method of treating a mammal to produce an anxiolytic or antipsychotic activity in said mammal.

According to the present invention, the foregoing and other objects are attained by providing a compound having the general formula (I):

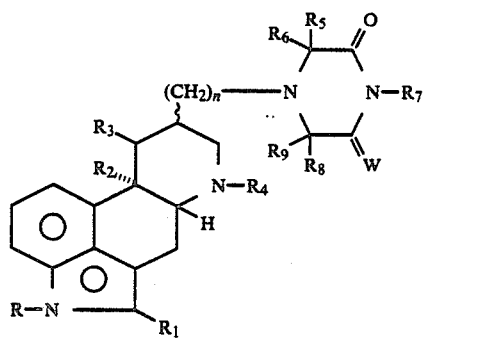

wherein R represents a hydrogen atom or a methyl group; $R_1$ represents a hydrogen or halogen atom, a methyl or phenylthio group or an alkylthio group having from 1 to 4 carbon atoms; either $R_2$ represents a hydrogen atom or a methoxy group and $R_3$ represents a hydrogen atom, or $R_2$ and $R_3$ together represent a chemical bond; $R_4$ represents a hydrocarbon group having from 1 to 4 carbon atoms; either each of $R_5$, $R_6$, $R_8$ and $R_9$ independently represents a hydrogen atom or an alkyl group having from 1 to 4 carbon atoms or $R_5$ and $R_8$ are as above defined and $R_6$ and $R_9$ together represent an ethylene or trimethylene group; $R_7$ represents a hydrogen atom, an alkyl group having from 1 to 4 carbon atoms, a phenyl group or a group of the general formula NR'R" wherein either each of R' and R" independently represents a hydrogen atom, an alkyl group having from 1 to 4 carbon atoms or an acyl group or R' and R" together with the nitrogen atom to which they are attached represent a heterocyclic ring; W represents an oxygen atom or two hydrogen atoms, and n is 0, 1 or 2; and pharmaceutically acceptable salts of such ergoline derivatives.

DESCRIPTION OF THE PREFERRED EMBODIMENTS

The present invention provides ergoline derivatives having the formula (I):

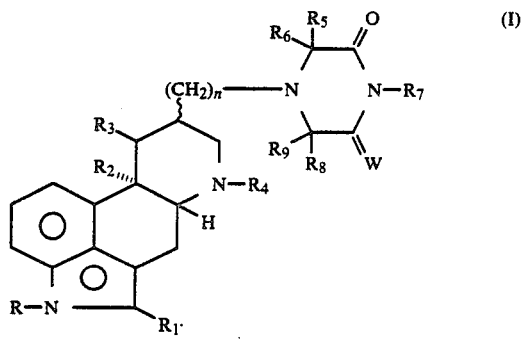

wherein R represents a hydrogen atom or a methyl group; $R_1$ represents a hydrogen or halogen atom, a methyl or phenylthio group or an alkylthio group having from 1 to 4 carbon atoms; either $R_2$ represents a hydrogen atom or a methoxy group and $R_3$ represents a hydrogen atom, or $R_2$ and $R_3$ together represent a chemical bond; $R_4$ represents a hydrocarbon group having from 1 to 4 carbon atoms; either each of $R_5$, $R_6$, $R_8$ and $R_9$ independently represents a hydrogen atom or an alkyl group having from 1 to 4 carbon atoms or $R_5$ and $R_8$ are as above defined and $R_6$ and $R_9$ together represent an ethylene or trimethylene group; $R_7$ represents a hydrogen atom, an alkyl group having from 1 to 4 carbon atoms, a phenyl group or a group of the general formula NR'R" wherein either each of R' and R" independently represents a hydrogen atom, an alkyl group having from 1 to 4 carbon atoms or an acyl group or R' and R" together with the nitrogen atom to which they are attached represent a heterocyclic ring; W represents an oxygen atom or two hydrogen atoms; and n is 0, 1 or 2; and pharmaceutically acceptable salts of such ergoline derivatives.

In the general formula halogen should be construed to preferably encompass chlorine and bromine atoms. However, halogen also encompasses fluorine.

In the definition of $R_4$, a hydrocarbon group having from 1 to 4 carbon atoms is intended to include alkyl, cycloalkyl and unsaturated (both ethylenically and acetylenically) groups. Representative moieties include methyl, ethyl, n-propyl, isopropyl, butyl, t-butyl, isobutyl, methylcyclopropyl, allyl and propargyl. An alkyl group having from 1 to 4 carbon atoms is preferably methyl, ethyl, n-propyl, isopropyl or n-butyl group, most preferably a methyl group.

In the definition of R' and R", an acyl group is intended to include $C_1$-$C_5$ alkanoyl and benzoyl groups. When R' and R" together with the nitrogen atom to which they are bonded form a heterocyclic ring, this ring is preferably selected from the group consisting of pyrrolidine, piperidine, morpholine, pyrazole, imidazole and pyrrole.

Although the pharmaceutically acceptable counterion which may be associated with the ergoline derivatives of this invention is not specifically limited, it may be, for example, a halide such as chloride or bromine; a mineral acid ion such as phosphate or sulfate; or an anion from a weak organic acid such as citrate, tartrate, acetate, etc.

The invention further provides a process for the preparation of the ergoline derivatives of the general formula I as above defined. The process comprises condensing an ergoline derivative of the general formula II with a piperazine derivative of the general formula III

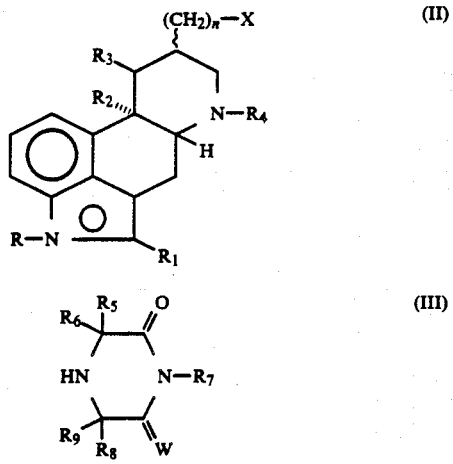

wherein R, $R_1$, $R_2$, $R_3$, $R_4$, $R_5$, $R_6$, $R_7$, $R_8$, $R_9$, W and n are as above defined and X represents a chlorine or bromine atom or a mesyloxy or tosyloxy group.

The condensation process is carried out in an organic solvent such as toluene, xylene, acetonitrile, dimethylformamide or dimethylsulphoxide in the presence of a catalytic amount of a catalyst such as potassium or sodium iodide at temperature of from 80° C. to 150° C. for a period of from 2 to 24 hours. The reaction may be carried out with an excess of the piperazine derivative which acts as an acid scavenger or with equimolar amounts of the reactants using an acid scavenger such as an inorganic carbonate or triethylamine.

When the reaction is complete the solvent is evaporated off and the residue is purified by crystallization or chromatography according to well known techniques.

The compounds of the general formula II and III are well known in the art or can be made from precursor compounds by well known reactions.

The ergoline derivatives according to the invention and their pharmaceutically acceptable salts are useful anxiolytic and antipsychotic agents and exhibit from moderate to good anti-hypertensive activity.

Profiles of the central sedative pharmacological activity were obtained by Irwin's observational assessment of mouse behavior (Irwin, S.—Psychopharmacologia, Berl., 13, 222, 1968), which also gives an indication of the orientative acute toxicity after 7 days observation, and by antagonism to the central apomorphine-induced stereotypes (climbing) in mice.

The results obtained with some compounds of the invention are reported in Table I

TABLE I

| Compound of Example No. | Apomorphine antagonism ($ED_{50}$, mg/kg p.o.) | Orientative acute toxicity ($LD_{50}$, mg/kg p.o.) |
|---|---|---|
| 1 | 4.4 | 600 |

TABLE I-continued

| Compound of Example No. | Apomorphine antagonism ($ED_{50}$, mg/kg p.o.) | Orientative acute toxicity ($LD_{50}$, mg/kg p.o.) |
|---|---|---|
| 2 | 0.9 | 300 |
| 3 | 2.2 | 300 |
| 5 | 0.5 | 200 |

For the antagonism to central apomorphine-induced climbing (Protais, P. et al.—Psychopharmacology, 50, 1, 1976), the compounds were orally administered to male mice, in a dose range between 0.25 and 10 mg/kg, 60 minutes before the subcutaneous injection of 1 mg/kg of apomorphine HCl. The antagonism to apomorphine-induced climbing behavior was evaluated 10 minutes after apomorphine administration.

The compounds of the invention also proved inactive in the induction of muscle relaxation (Irwin's test in the mouse) and motor incoordination (Rotarod test in the rat as described by Dunham, N. W. et al.—J. Am. Pharm. Assn. 46:208, 1957) up to an oral dose of 10 mg/kg.

Accordingly, the invention further provides a pharmaceutical composition comprsing an ergoline derivative having the general formula I or a pharmaceutically acceptable salt thereof in admixture with a pharmaceutically acceptable diluent or carrier.

Compounds of formula I and their salts described herein may be administered by parenteral or oral route, preferably by oral route.

Depending on administration route, the compositions may be in the form of solid, semi-solid or liquid dosage form, such as, for example, tablets, pills, capsules, powders, liquids, suspensions or the like.

The composition will include a conventional pharmaceutical carrier or excipient and an active compound of formula I or the pharmaceutically acceptble salt thereof and, in addition, may include other medicinal agents, pharmaceutical agents, carriers, adjuvants, etc.

The dosage of the present drugs varies in accordance with the sex, age, condition or medical record of the patient, as well as according to the route or purpose of the administration. In general, the drugs may be administered as single doses or as divided doses so as to provide, for example, about 0.001–5 mg/kg body weight per day of effective ingredient, preferably about 0.005–1 mg/kg body weight.

The pharmaceutical compositions containing the compounds of the invention are prepared according to conventional methods with the usual ingredients.

Thus, for oral administration, the pharmaceutical compositions containing the compounds of the invention are preferably tablets, pills or capsules which contain the active substance together with diluents, such as, for example, lactose, dextrose, sucrose, mannitol, sorbitol, sucrose, cellulose; lubricants, for instance, silica, talc, stearic acid, magnesium or calcium stearate and/or polyethylene glycols; or they may also contain binders, such as, for example, starches, gelatin, methyl-cellulose, gum-arabic, tragacanth, polyvinylpyrrolidone; disintegrating agents, such as, for instance, starches, alginic acid, alginates; effervescing mixtures; dyestuffs; sweeteners; wetting agents, such as, for instance, lecithin, polysorbates, laurylsulphates; and, in general, non-toxic and pharmacologically inactive substances used in pharmaceutical formulations.

The pharmaceutical preparations may be manufactured in a known manner, for example, by means of mixing, granulating, tabletting, sugar-coating, or film-coating processes. Also, the other pharmaceutical formulations containing the compounds of the invention may be prepared by known methods and they can be, for example, a syrup or drops for oral administration, sterile solutions for injection, or suppositories.

Each and every publication, patent or otherwise, specifically identified in this specification represents a teaching of the understanding of those skilled in the art at the time this invention was made and is herein individually incorporated by reference to the same extent as if it had been physically reproduced in the location and for the purpose as identified by the context in which it is found.

The invention will now be further described by specific examples which are intended to illustrate the present invention and are not intended to limit the same.

EXAMPLE 1

6-Methyl-8β-(3,5-dioxo-piperazin-1-ylmethyl)-ergoline (I: $R=R_1=R_2=R_3=R_5=R_6=R_7=R_8=R_9=H$, $R_4=CH_3$, $W=O$, $n=1$)

A solution of 4.1 g of 6-methyl-8β-tosyloxymethyl-ergoline, 2.2 g of piperazine-3,5-dione and 0.2 g of potassium iodide in 80 ml of dimethylformamide was heated at 80° C. for 5 hours. The dimethylformamide was evaporated off; the residue, dissolved in methylene dichloride, was washed with water and saline and dried over anhydrous sodium sulphate. After filtration and removal of the solvent, the product was crystallized from methanol to give 2.8 g of the title compound, m.p. 260°–262° C.

EXAMPLE 2

1,6-Dimethyl-8β-(3,5-dioxo-piperazin-1-ylmethyl)-ergoline (I: $R_1=R_2=R_3=R_5=R_6=R_7=R_8=R_9=H$, $R=R_4=CH_3$, $W=O$, $n=1$)

Operating as in Example 1, but employing 1,6-dimethyl-8β-tosyloxymethyl-ergoline in place of 6-methyl-8β-tosyloxymethyl-ergoline, the title compound, m.p. 268°–270° C., was obtained in 80% yield.

EXAMPLE 3

6-Methyl-8β-(3,5-dioxo-4-methyl-piperazin-1-ylmethyl)-ergoline (I: $R=R_1=R_2=R_3=R_5=R_6=R_8=R_9=H$, $R_4=R_7=CH_3$, $W=O$, $n=1$)

Operating as in Example 1, but employing 4-methyl-piperazine-3,5-dione in place of piperazine-3,5-dione, the title compound, m.p. 235°–237° C., was obtained in 75% yield.

EXAMPLE 4

6-Methyl-8β-(3,5-dioxo-4-amino-piperazin-1-ylmethyl)-ergoline

I: $R=R_1=R_2=R_3=R_5=R_6=R_8=R_9=H$, $R_4=CH_3$, $R_7=NH_2$, $W=O$, $n=1$)

Operating as in Example 1, but employing 4-amino-piperazine-3,5-dione in place of piperazine-3,5-dione, the title compound, m.p. 210°–212° C., was obtained in 65% yield.

EXAMPLE 5

6-Methyl-9,10-didehydro-8β-(3,5-dioxo-piperazin-1-ylmethyl)-ergoline (I: $R=R_1=R_5=R_6=R_7=R_8=R_9=H$, $R_2+R_3$=chemical bond, $R_4=CH_3$, $W=O$, $n=1$)

Operating as in Example 1, but employing 9,10-didehydro-6-methyl-8β-tosyloxymethyl-ergoline in place of 6-methyl-8β-tosyloxymethyl-ergoline, the title compound, m.p. 208°–210° C., was obtained in 68% yield.

EXAMPLE 6

6-Methyl-8β-(3-oxo-piperazin-1-ylmethyl)-ergoline (I: $R=R_1=R_2=R_3=R_5=R_6=R_7=R_8=R_9=H$, $R_4=CH_3$, $W=H_2$, $n=1$)

Operating as in Example 1, but employing piperazine-2-one in place of piperazine-3,5-dione, the title compound, m.p. 238°–240° C., was obtained in 75% yield.

EXAMPLE 7

6-Methyl-9,10-didehydro-8β-(3,5-dioxo-4-amino-piperazin-1-ylmethyl)-ergoline (I: $R=R_1=R_5=R_6=R_8=R_9=H$, $R_2+R_3$=chemical bond, $R_4=CH_3$, $R_7=NH_2$, $W=O$, $n=1$)

Operating as in Example 5, but employing 4-amino-piperazine-3,5-dione in place of piperazine 3,5-dione, the title compound, m.p. 224°–226° C., was obtained in 62% yield.

EXAMPLE 8

6-Methyl-8β-(3,5-dioxo-4-phenyl-piperazin-1-ylmethyl)-ergoline)

(I: $R=R_1=R_2=R_3=R_5=R_6=R_8=R_9=H$, $R_4=CH_3$, $R_7$=phenyl, $W=O$, $n=1$)

Operating as described in Example 1, but employing 4-phenyl-piperazine 3,5-dione in place of piperazine 3,5-dione, the title compound, m.p. 260°–262° C., was obtained in 70% yield.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An ergoline compound of the formula I

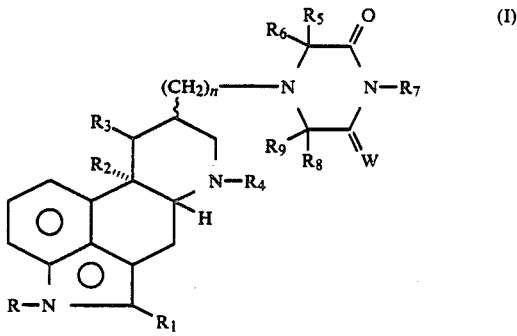

wherein

R represents a hydrogen atom or a methyl group;

$R_1$ represents a hydrogen or halogen atom, a methyl or phenylthio group or an alkylthio group having from 1 to 4 carbon atoms;

$R_2$ represents a hydrogen atom or a methoxy group and $R_3$ represents a hydrogen atom, or $R_2$ and $R_3$ together represent a chemical bond;

$R_4$ represents a hydrocarbon group having from 1 to 4 carbon atoms selected from the group consisting of alkyl, cycloalkyl, and ethylenically or acetylenically unsaturated groups;

$R_5$, $R_6$, $R_8$ and $R_9$ each independently represents a hydrogen atom or an alkyl group having from 1 to 4 carbon atoms, or $R_5$ and $R_8$ are as above defined and $R_6$ and $R_9$ together represent an ethylene or trimethylene group;

$R_7$ represents a hydrogen atom, an alkyl group having from 1 to 4 carbon atoms, a phenyl group or a group of the general formula NR'R" wherein either each of R' and R" independently represents a hydrogen atom, an alkyl group having from 1 to 4 carbon atoms or an acyl group selected from the group consisting of $C_{1-5}$ alkanoyl and benzoyl groups, or R' and R" together with the nitrogen atom to which they are attached represent a heterocyclic ring selected from the group consisting of pyrrolidine, piperidine, morpholine, pyrazole, imidazole and pyrrole;

W represents an oxygen atom or two hydrogen atoms; and n is 0, 1 or 2;

and pharmaceutically acceptable salts of a compound of formula I.

2. The compound of claim 1, which is 6-methyl-8β-(3,5-dioxo-piperazin-1-ylmethyl)-ergoline.

3. The compound of claim 1, which is 1,6-dimethyl-8β-(3,5-dioxo-piperazin-1-ylmethyl)-ergoline.

4. The compound of claim 1, which is 6-methyl-8β-(3,5-dioxo-4-methyl-piperazin-1-ylmethyl)-ergoline.

5. The compound of claim 1, which is 6-methyl-8β-(3,5-dioxo-4-amino-piperazin-1-ylmethyl)-ergoline.

6. The compound of claim 1, which is 6-methyl-9,10-didehydro-8β-(3,5-dioxo-piperazin-1-ylmethyl)-ergoline.

7. The compound of claim 1, which is 6-methyl-8β-(3-oxo-piperazin-1-ylmethyl)-ergoline.

8. A pharmaceutical composition which exerts anxiolytic, hypotensive or neuroleptic activity comprising an ergoline derivative according to claim 1 or a pharmaceutically acceptable salt of said ergoline derivative in admixture with a pharmaceutically acceptable diluent or carrier, wherein the amount of said ergoline derivative in said composition in sufficient to exert anxiolytic, neuroleptic or anti-hypertensive activity in a mammal.

9. A method for treating anxiety in humans, which comprises administering to a subject in need of such treatment a therapeutically effective amount of a compound of claim 1 or a pharmaceutically acceptable salt thereof.

10. The pharmaceutical composition of claim 8, wherein said amount of said ergoline compound is from about 0.001 to 5 mg/kg of body weight of said mammal.

11. The pharmaceutical composition of claim 8, wherein said amount of said ergoline compound is from about 0.005 to 1 mg/kg of body weight of said mammal.

12. A method of treating a mammal to produce an anxiolytic or neuroleptic activity in said mammal, wherein said mammal is one in need of said treatment, which comprises administering to said mammal a pharmaceutically effective amount of a composition according to claim 8.

13. The method of claim 12, wherein said amount is from 0.001 to 5 mg/kg of body weight of said mammal.

14. The method of claim 12, wherein said amount is from 0.005 to 1 mg/kg of body weight of said mammal.

15. The method of claim 12, wherein said mammal is a human.

16. A method for exerting a neutroleptic effect in humans, which comprises administering to a subject in need of such effect a therapeutically effective amount of a compound of claim 1 or a pharmaceutically acceptable salt thereof.

* * * * *